(12) United States Patent
Crockett

(10) Patent No.: US 11,406,779 B2
(45) Date of Patent: Aug. 9, 2022

(54) AUTOMATIC TRACHEOTOMY DEVICE

(71) Applicant: Kathy Crockett, Columbia, VA (US)

(72) Inventor: Kathy Crockett, Columbia, VA (US)

(*) Notice: Subject to any disclaimer, the term of this patent is extended or adjusted under 35 U.S.C. 154(b) by 313 days.

(21) Appl. No.: 16/793,057

(22) Filed: Feb. 18, 2020

(65) Prior Publication Data

US 2022/0088334 A1 Mar. 24, 2022

(51) Int. Cl.
*A61M 16/04* (2006.01)

(52) U.S. Cl.
CPC .... *A61M 16/0472* (2013.01); *A61M 16/0497* (2013.01); *A61M 2205/3344* (2013.01); *A61M 2205/3375* (2013.01); *A61M 2205/50* (2013.01); *A61M 2205/581* (2013.01); *A61M 2205/584* (2013.01)

(58) Field of Classification Search
CPC .......... A61M 16/0472; A61M 16/0497; A61M 16/0465; A61M 16/0402; A61M 2005/14252; A61M 2005/1585
See application file for complete search history.

(56) References Cited

U.S. PATENT DOCUMENTS

| | | | |
|---|---|---|---|
| 7,373,939 B1 | 5/2008 | DuBois et al. | |
| 11,129,952 B1* | 9/2021 | Pollack | A61M 16/0472 |
| 2016/0227991 A1 | 8/2016 | Hayut | |
| 2020/0179631 A1* | 6/2020 | Sarkar | A61M 16/0472 |

* cited by examiner

Primary Examiner — Nathan R Price
Assistant Examiner — Courtney B Fredrickson
(74) Attorney, Agent, or Firm — Sanchelima & Associates, P.A.; Christian Sanchelima; Jesus Sanchelima

(57) ABSTRACT

An automatic tracheotomy/cricothyrotomy device is disclosed herein. This device includes a hand-held apparatus having a box shaped center apparatus (box) with a removable attached handlebar (handlebar). The handlebar includes two handles and top and bottom center bars. The handlebar contains four receiver clips. The box contains clip locks that secure the box onto the handlebar. Additionally, the box contains a capacitance measuring system for locating specific portions of the trachea, a peel-off cover that exposes a cleansing pad and adhesive backed flange. The flange has ribbons for securing the tube in a patient's neck. The box also contains pressure and locator sensors with corresponding indicator lights/sounds. The center box also contains a mechanism for penetrating the tracheal cartilage or medial cricothyroid membrane while simultaneously inserting a tube member. The mechanism retracts the puncture obturator back into the box leaving the tube inserted. Securing ribbons are exposed then placed around a patient's neck.

11 Claims, 5 Drawing Sheets

AUTOMATIC TRACHEOTOMY DEVICE

BACKGROUND OF THE INVENTION

1. Field of the Invention

The present invention relates to a tracheotomy device and, more particularly, to a tracheotomy/cricothyrotomy device that automates the process of properly inserting a tracheotomy tube into a user's trachea.

2. Description of the Related Art

Several designs for a tracheotomy device have been designed in the past. None of them, however, include a tracheotomy/cricothyrotomy device comprising a hand-held apparatus having a box-shaped center apparatus with a removable attached handlebar which has two handles attached to a top and bottom center bar wherein the box shaped center apparatus contains a capacitance measuring system for locating specific portions of the trachea. The center portion contains a mechanism for penetrating the trachea and inserting a tube member. The handlebar and the center apparatus clip together using four clips positioned in the corners of the center apparatus. It is known that certain individuals are often in desperate need of an airway in order to breath. A tracheotomy or cricothyrotomy are procedures that either puncture the airway or cut into the airway to insert a breathing tube within a user's trachea in order to create a proper air way to allow the individual to breathe. These procedures are normally only performed by professional medical personnel qualified to make the incision or puncture needed to then insert the tracheotomy tube.

However, in an event of an emergency, professional medical personnel may not be available, thereby putting the life of an individual in danger if they are in need of a proper and immediate airway. Therefore, there is a need for an automatic tracheotomy device that automates the process of inserting a tracheotomy device within a trachea to provide easy access to establish an airway. The device will make inserting a tracheotomy device a simple and easy task that can save many lives and lessens operator error during emergency and non-emergency use.

Applicant believes that a related reference corresponds to U.S. Pat. No. 7,373,939 issued for a tool for performing a tracheotomy that includes a trocar and a delivery mechanism for a stoma stent. Applicant believes another related reference corresponds to U.S. patent No. 2016/0227991 issued for a system for guiding the insertion of an endotracheal intubation tube using an optical sensor and an autonomous modulated light source. However, the present invention differs from these references because they fail to disclose a handheld apparatus having a box-shaped center apparatus with a removable handlebar which has two handles attached to a top and a bottom center bar. Additionally, the box-shaped center apparatus contains a capacitance measuring system for locating specific portions of the trachea either in the medial cricothyroid membrane or tracheal cartilage. The center portion contains a mechanism for penetrating the medial cricothyroid membrane or tracheal cartilage depending on desired placement and simultaneously inserting a tube member then automatically removing the puncture obturator leaving the tube in place to be secured by ribbon. The handlebar and the center apparatus clip together using four clips positioned in the corners of the center apparatus. The present invention addresses these issues by providing a tracheotomy/cricothyrotomy device that automizes the process of inserting the tracheotomy tube. Additionally, the present invention includes a combination of two sensors, one for location and one for pressure, to further aid a user in proper operation of the automatic tracheotomy/cricothyrotomy device and corresponding light emitting diodes (LEDs) or some other type of light that will be connected to the sensors. Sounding beeps will reinforce these light sensors indicating proper placement and pressure. A peel off cleaning pad and adhesive backed flange are also important features not in the above patent. The operator peels off a cover exposing the cleaning pad; during placement on the patients neck it swabs the area cleaning and disinfecting to decrease chance of infection. Also, when the operator peels off the cover it exposes an adhesive backed trach flange that will stick to the patients neck long enough to be secured with attached ribbons when the trach tube is inserted it clicks into the flange and the puncture obturator is withdrawn back into the box.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide an automatic tracheotomy device that automizes the process of inserting a tracheotomy tube within an easy to operate sterile housing.

It is another object of this invention to provide an automatic tracheotomy/cricothyrotomy device that includes a pressure sensor and an ultrasonic or ultrasound sensor to aid a user in proper positioning and pressure to exert.

It is another object of this invention to provide an automatic tracheotomy/cricothyrotomy device that when in a proper position a positional indicator light will turn green.

It is another object of this invention to provide an automatic tracheotomy/cricothyrotomy device that when the requisite pressure upon the throat is exerted the pressure indicator will also turn green.

It is another object of this invention that when the user holds the device in place for three seconds more or less and when both indicator lights are green, the tube/obturator will automatically inject into the airway, click into a flange and the obturator will automatically retract back into box leaving the tracheotomy tube in place.

It is another feature of this invention to provide an automatic tracheotomy/cricothyrotomy device that when both indicator lights turn green a sound is emitted to show proper placement and pressure.

It is still another object of the present invention to provide an automatic tracheotomy device that includes a re-useable handlebar than can be sterilized and that provides ease of use for user operating the device. Another box may be simply clicked back into the frame.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
FIG. 1 represents an operational view of automatic tracheotomy device 10 in accordance to an embodiment of the present invention.
Figure 2:
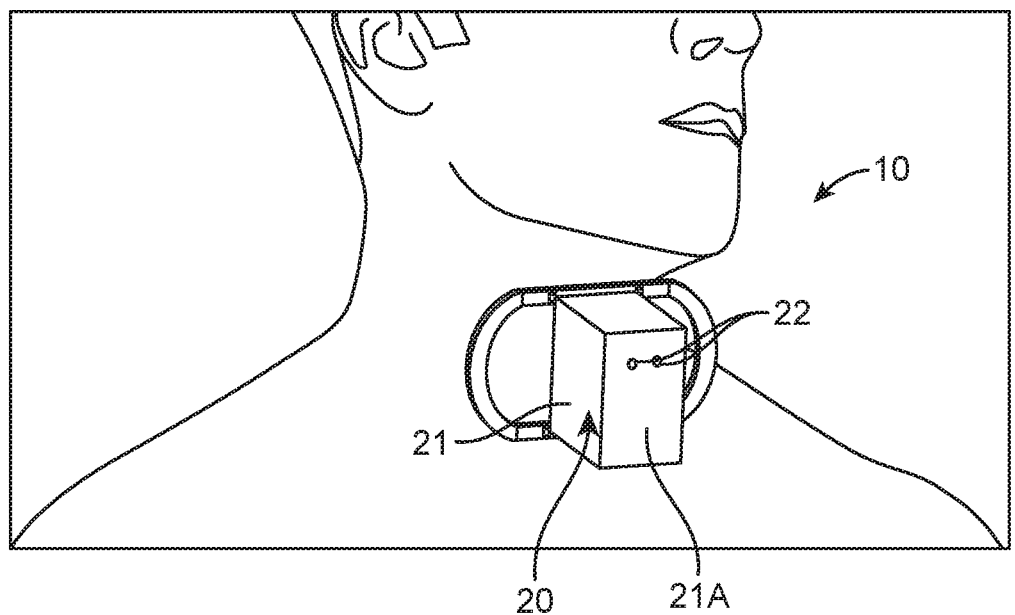
FIG. 2 illustrates an enlarged isometric view of automatic tracheotomy device 10 being placed on a patient's neck.
Figure 3:
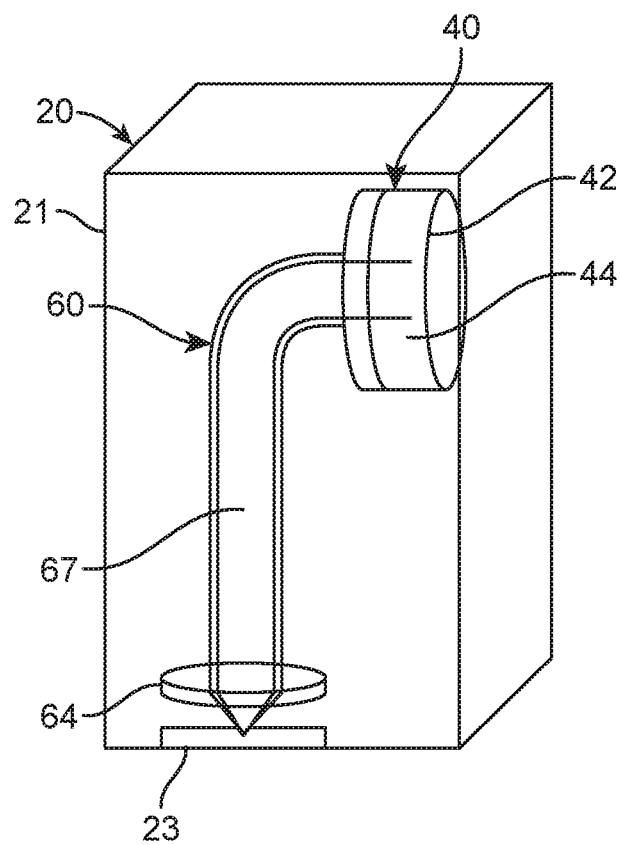
FIG. 3 shows an isometric internal side view of handheld assembly 20 in accordance to an embodiment of the present invention having motor assembly 40 therein.
Figure 4:
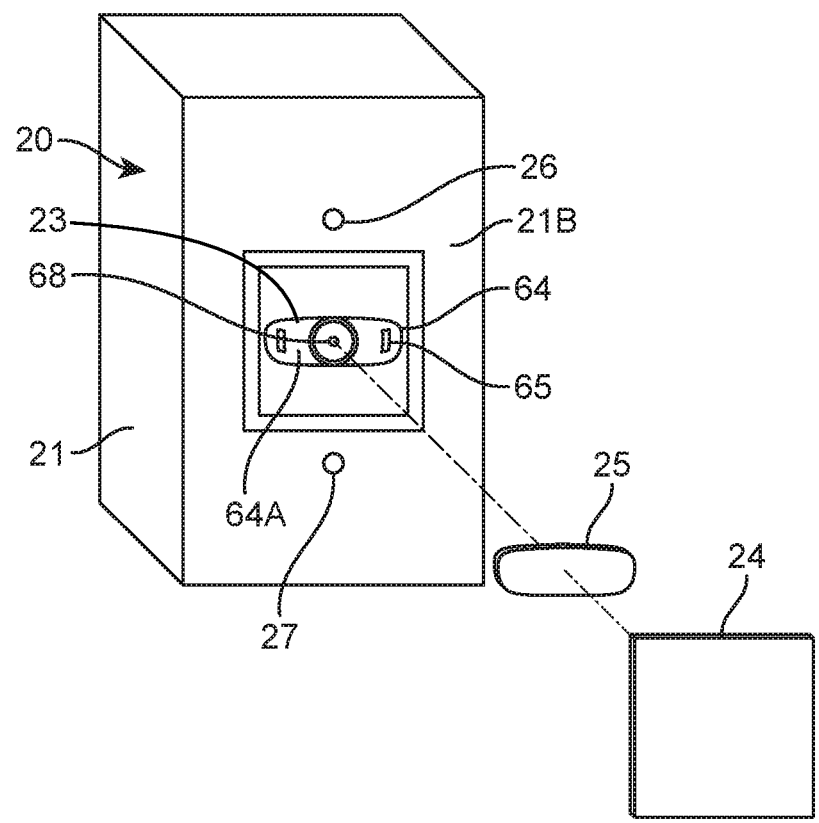
FIG. 4 illustrates an isometric rear view of handheld assembly 20 in accordance to an embodiment of the present invention.
Figure 5:
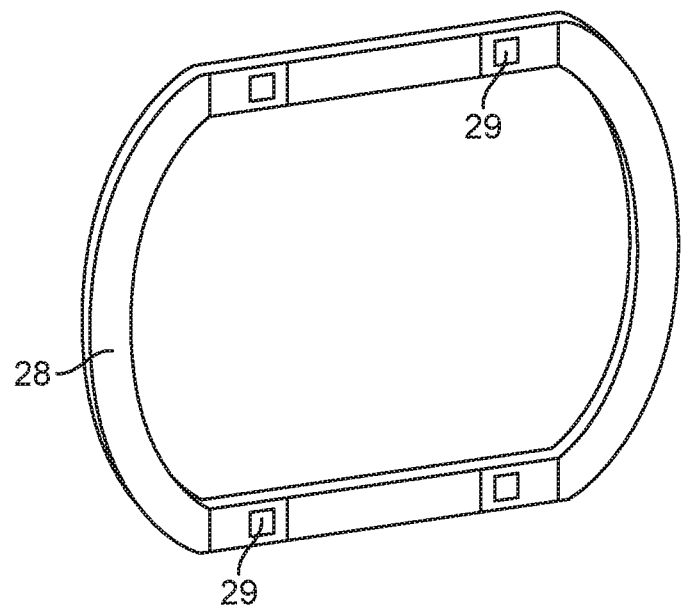
FIG. 5 is a representation of handlebar frame 28 of handheld assembly 20 in accordance to an embodiment of the present invention.
Figure 6:
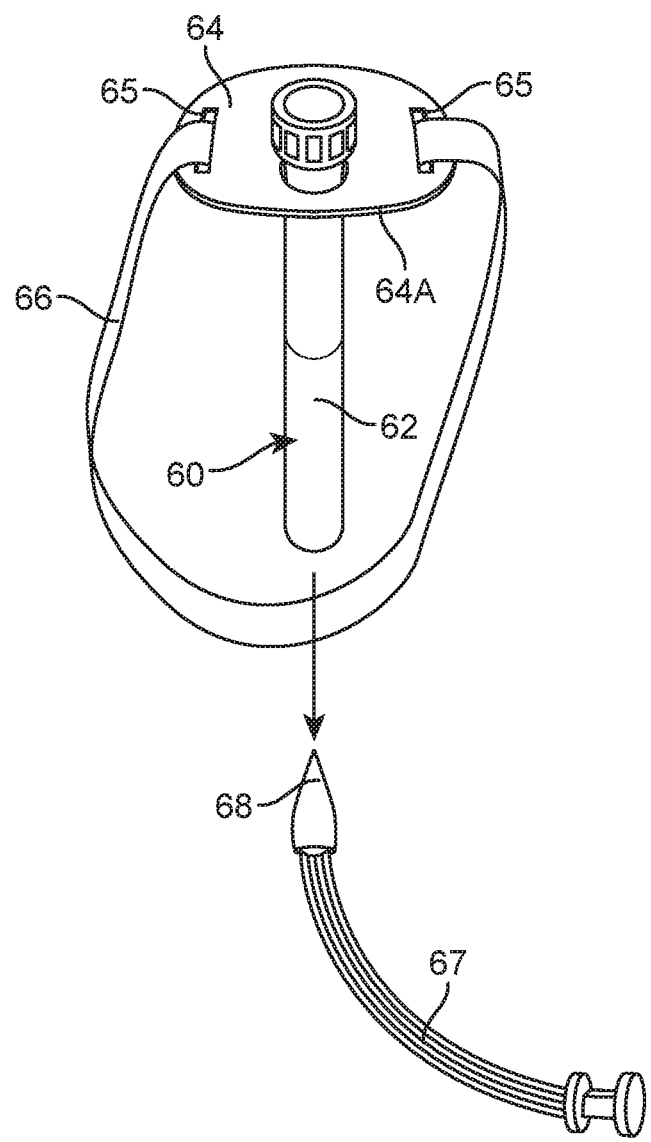
FIG. 6 shows an exploded view of tracheotomy assembly 60 in accordance to an embodiment of the present invention.
Figure 7:
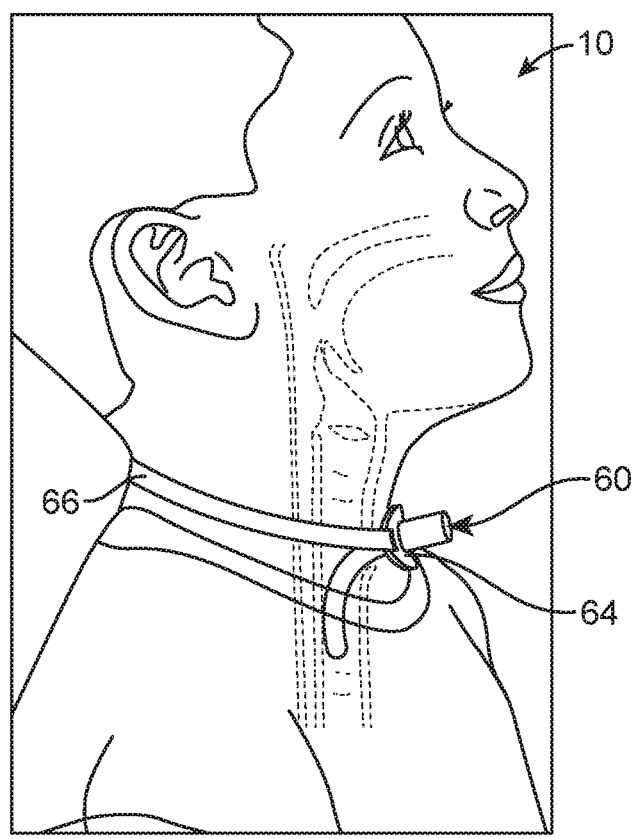
FIG. 7 illustrates an isometric view of tracheotomy assembly 60 inserted within a patient's trachea in accordance to an embodiment of the present invention.

Referring now to the drawings, where the present invention is generally referred to with numeral 10, it can be observed an automatic tracheotomy/cricothyrotomy device 10 that includes a handheld assembly 20, a motor assembly 40, and tracheotomy assembly 60.

Handheld assembly 20 includes a center apparatus being a box 21 having a front end 21A and a back end 21B. In one embodiment, box 21 is a cubic rectangular housing made of a suitable material made of high-grade plastic or aluminum. It should be understood, box 21 may be made of other suitable materials and may come in other suitable shapes. Additionally, box 21 houses motor assembly 40 and tracheotomy assembly 60 therein. In one embodiment, front end 21A includes at least two LEDs 22 mounted thereon. LEDs 22 may be mounted near a top end of front end 21. Additionally, LEDs 22 may be of any suitable color that may be used to alert a user. This may include colors such as but not limited to red, green, and the like. Front end 21A may further include indicia etched thereon. This indicium may include instructions regarding the operational use of automatic tracheotomy device 10. Back end 21B includes an opening 23 located on a center portion thereon. In one embodiment, opening 23 may be a rectangular opening positioned on a center portion of back end 21B. Additionally, opening 23 may be covered by a peel-off cover 24. Peel-off cover 24 may be a rectangular sheet having an adhesive material one side. Additionally, peel-off cover 24 may further have dimensions such that it covers and surrounds the entirety of the opening 23. Furthermore, a peel-off cover 24 may further enclose a cleaning pad 25 within opening 23 so that during positioning of the device the area is cleaned to reduce infection. In one embodiment, cleaning pad 25 includes a disinfectant substance on it to properly clean a patient's neck area while positioning/operating automatic tracheotomy device 10. This disinfectant substance may be a chlorhexidine substance, although other substances may be used. The peel-off cover also exposes a flange of a trach tube which has adhesive to temporarily hold the trach tube in place during and after obturator punctures into patient airway. A ribbon or string of some type is then used to tie the tracheostomy device around the patient's neck after insertion. Other securement means may also be used.

Back end 21B of box 21 may further include a pressure sensor 26 and an ultrasonic or ultrasound sensor 27 adapted to aid a user in locating specific portions of a patient's trachea. In one embodiment, pressure sensor 26 and ultrasonic or ultrasound sensor 27 may be provided as hardware within box 21. Additionally, both sensors may be located above and below opening 23. Pressure sensor 26 aids in notifying the user if they are applying the correct amount of pressure on a user's neck to be able to actuate automatic tracheotomy/cricothyrotomy device 10. Additionally, ultrasonic or ultrasound sensor 27 aids a user in identifying the specific portions of a patient's trachea that is to be penetrated either in the medial cricothyroid membrane or between the tracheal rings into the tracheal cartilage. In one embodiment, automatic tracheotomy device 10 will not be deployed until each sensor locates a pre-determined value. Once the correct location is found, box 21 may be configured to provide an audible solid tone. Additionally, LEDs 22 may then light up into a green color thereby indicating that tracheotomy assembly 60 is then ready to be deployed. In one embodiment, tracheotomy device assembly 60 may be automatically deployed once both LEDs are both turned green and a three-second time period has lapsed. It should be understood, additional embodiments may include further combinations of other sensors to ensure that the safest location for puncturing is located for automatic tracheotomy device 10.

Handheld assembly 20 further includes a handlebar frame 28 that may be attached to box 21. In one embodiment, handlebar frame 28 is a frame having four perimeter sides. Additionally, handlebar frame 28 may include two horizontal frame members and two vertical semi-circular members. As a result, of this configuration and elongated oval shape may be formed. It should be understood, other shapes of frames may be used for handlebar frame 28. Furthermore, handlebar frame 28 may also include four clips 29 mounted near four corners of handlebar frame 28. In one embodiment, clips 29 may be of a magnetic variety. Clips 29 may also be any other removable attachment member shown in the art such as hook and loop fasteners or clip and lock, press and lock adhesives, and the like. Clips 29 receive four corners of box 21 in order to create a secure attachment thereon. The circular portions of the frame remain exposed such that a user may effectively control automatic tracheotomy device 10 with both hands. In one embodiment, automatic tracheotomy device 10 may be operated without handlebar frame 28. As a result, there may be two possible variations of automatic tracheotomy device 10. In one variation, the device is provided absent of handlebar frame 28. This variation may be an easily disposable version meant to be used as an emergency variation of the device used for personal or military use. The other possible variation includes automatic tracheotomy device 10 having handlebar frame 28. In this variation a user may continuously re-use handlebar frame 28 and continuously purchase box/cartridge 21 to then be fitted into handlebar frame 28. This variation may be used by hospitals to aid staff in properly and easily inserting tracheotomy assembly 60 to patients in need, weather for surgery or emergency. A one-time use frame with a sterile stationary box 21 is also a variation. Box 21 may be disposed of in a sharp's container. Additionally, box 21 is sterile and ready for use.

Motor assembly includes a motor 42 and a processor 44 housed within box 21. In one embodiment, tracheotomy assembly 60 is communicably attached to motor 42 to be properly actuated into a patient. Processor 44 allows for the control of the various components hosed within box 21. In one embodiment, pressure sensor 26 and ultrasonic or ultrasound sensor 27 are communicably attached to processor 44. Processor 44 then receives the information gathered by both sensors and then determines if motor 42 should be actuated to then insert tracheotomy assembly 60 and a tube 62 within a patient. In one embodiment, processor 44 provides lighting to one of the LEDs once an appropriate amount of pressure has been detected. This allows a user to acknowledge that they are applying the appropriate amount of pressure onto a patient's throat area to allow tracheotomy assembly 60 to be properly inserted. Additionally, processor 44 may also provide lighting to one of LEDs 22 once an appropriate location of a patient's trachea has been sensed by ultrasonic or ultrasound sensor 27. This further allows a user to acknowledge that have located the appropriate location for tracheotomy assembly 60 to then be inserted into the patient's trachea. Once both of the LED 22 lights have been actuated, a predetermined amount of time will pass (such as 3 seconds), and processor 44 will then actuate motor 42 to then insert tracheotomy assembly 60 within the patient's trachea.

Tracheotomy assembly 60 is enclosed within box 21 and includes a tube 62, a snap in flange 64, and an obturator 67. In one embodiment, tracheotomy assembly 60 is one of the many variations of tracheostomy devices in the market that is fitted within box 21. It should be understood, any suitable tracheotomy device may be used within the tracheotomy assembly 60 and is not limited to being the one seen in the figures of this disclosure. In one embodiment, flange 64 may be oval in shape and slip mounted onto tube 62 with the ability to automatically clip into place when tube 62 is inserted into a patent's airway. Additionally, flange 64 may include an adhesive side 64A being exposed. When peel-off cover 24 is removed, adhesive side 64A allows flange 64 to be temporarily attached to a user's throat to aid in the secure placement of tracheotomy assembly 60. A ribbon 66 may then be tied around the neck of a user to secure the tube 62 to a patient. Obturator 67 is housed within tube 62. Additionally, obturator 67 includes a puncture tip 68 to aid in creating an opening in a patient's trachea. In one embodiment, puncture tip 68 may be a conical member located at a distal end of obturator 67. Additionally, box 21 may then be positioned over a patient's throat. Once processor 44 triggers tracheotomy assembly 60, obturator 67 then punctures a patient's trachea and simultaneously inserts tube 62 therein. Once inserted, the tube clicks into the flange 64 and obturator 67 is then automatically retracted from the tube 62 within the patients neck into box 21 by motor 42 housed therein. The user then ties the ribbon around a user's neck. As a result, a safe and secure airway is created for a patient. Automatic tracheotomy/cricothyrotomy device 10 automates the process of inserting a tracheotomy device within a user's trachea. It is a safe and easy to use device, that could potentially save many lives. Individuals that find themselves in need of a tracheotomy/cricothyrotomy whether for placement before or during surgery or an emergency or battlefield situation will benefit from this device.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense

What is claimed is:

1. An automatic tracheotomy/cricothyrotomy device, comprising:

a. a handheld assembly including a center apparatus being a box having a cubic-rectangular shape, wherein said box includes a front end and a back end, said front end including two light emitting diodes (LEDs) mounted thereon, said back end having a rectangular opening positioned on a center portion, wherein said back end further includes at least one pressure sensor and at least one ultrasonic or ultrasound sensor adapted to locate specific portions of a patient's trachea, wherein said at least one pressure sensor is located above said rectangular opening, wherein said at least one ultrasonic or ultrasound sensor is located below said rectangular opening, wherein said handheld assembly includes a handlebar frame having four perimeter sides, said handlebar frame including four clips mounted on four corners of said handlebar frame, wherein said four clips receive said back end of said box;
 b. a motor assembly including a motor housed within said box, wherein said motor is communicably attached to a processor within said box; and
 c. a tracheotomy assembly housed within said box including a tube, a flange with ribbons attached, and an obturator, wherein said flange is oval in shape and slip mounted on said tube, wherein said flange includes an adhesive side, said flange further including two side openings, wherein said obturator includes a puncture tip, said obturator being inserted within said tube, wherein said flange is positioned within said rectangular opening with said adhesive side being exposed, wherein said box is configured to be placed over a patient's throat and said motor is configured to actuate said obturator to puncture said patient's trachea and to insert said tube, thereby locking said tube into the flange, wherein said motor is further configured to retract said obturator and to leave said tube inserted within said patient's trachea.

2. The automatic tracheotomy/cricothyrotomy device of claim 1, wherein said rectangular opening is covered by a peel-off cover, wherein said peel-off cover is configured to be removed to expose said flange.

3. The automatic tracheotomy/cricothyrotomy device of claim 2 wherein said peel-off cover, when peeled off, provides a user with a cleaning pad laced with a cleaning solution, said cleaning pad is adapted to clean an area of the patient's throat as said automatic tracheotomy/cricothyrotomy device is being positioned thereon.

4. The automatic tracheotomy/cricothyrotomy device of claim 1 wherein said front end of said box includes indicia having instructions to operate said automatic tracheotomy/cricothyrotomy device thereon.

5. The automatic tracheotomy/cricothyrotomy device of claim 1 wherein said four perimeter sides include two horizontal frame members and two vertical semi-circular frame members.

6. The automatic tracheotomy/cricothyrotomy device of claim 1 wherein said two side openings of said flange receive the ribbon which is adapted to be tied around the patient's neck.

7. The automatic tracheotomy/cricothyrotomy device of claim 1 wherein said puncture tip is a conical member located at a distal end of said obturator.

8. The automatic tracheotomy/cricothyrotomy device of claim 1 wherein said at least one pressure sensor and said at least one ultrasonic or ultrasound sensor are communicably attached to said processor.

9. The automatic tracheotomy/cricothyrotomy device of claim 8 wherein said processor is configured to provide lighting to one of said LEDs with a corresponding audio alert once an appropriate amount of pressure has been sensed.

10. The automatic tracheotomy/cricothyrotomy device of claim 8 wherein said processor is configured to provide lighting to one of said LEDs with a corresponding audio alert once an appropriate location of the patient's trachea has been sensed.

11. An automatic tracheotomy device, comprising:
a. a handheld assembly including a center apparatus being a box having a cubic-rectangular shape, wherein said box includes a removably attached handlebar which has two handles attached to a top and a bottom center bar, wherein said box includes a pressure sensor and an ultrasonic or ultrasound sensor adapted to locate specific portions of a patient's trachea, wherein said handlebar frame and said box each include four corresponding clips located on each corner of said handlebar and said box to create a secure attachment; and
b. a motor assembly including a motor attached to a puncturing member within said box, wherein said puncturing member is adapted to penetrate a patient's trachea and insert a tube member therein, wherein said puncturing member is an obturator, wherein said obturator is configured to retract back into said box to then be disposed.

* * * * *